United States Patent
De Simone

(10) Patent No.: US 6,562,336 B2
(45) Date of Patent: May 13, 2003

(54) DIETARY OR PHARMACEUTICAL COMPOSITION FOR USE FOR THE PREVENTION OR TREATMENT OF HYPEROXALURIA

(75) Inventor: Claudio De Simone, Ardea (IT)

(73) Assignee: VSL Pharma Limited, Dublin (IR)

( * ) Notice: Subject to any disclaimer, the term of this patent is extended or adjusted under 35 U.S.C. 154(b) by 0 days.

(21) Appl. No.: 09/992,029

(22) Filed: Nov. 26, 2001

(65) Prior Publication Data

US 2002/0061292 A1 May 23, 2002

Related U.S. Application Data

(63) Continuation of application No. PCT/IT00/00213, filed on May 24, 1999.

(51) Int. Cl.$^7$ .................................................. C12N 1/00
(52) U.S. Cl. ............................... 424/93.44; 424/93.45; 424/93.3
(58) Field of Search ........................... 424/93.44, 93.45, 424/93.3

(56) References Cited

FOREIGN PATENT DOCUMENTS

| EP | 0 577 904 A1 | 1/1994 |
|----|--------------|--------|
| EP | 0 795 604 A2 | 9/1997 |
| EP | 0 856 259 A1 | 8/1998 |
| WO | WO 98/52586 | 11/1998 |

OTHER PUBLICATIONS

Ito, Haruo; "Urolithiasis and Oxalate Metabolism"; Nippon Hinyokika Gakkai Zasschi; vol. 88, 1997, pp. 701–711; XP000971627; figure 13.

Ito, H. et al; "Reduction of Oxalate Content of Foods by the Oxalate Content Degrading Bacterium Eubacterium Lentum WYH–1"; INT. J. Urology; vol. 3, No. 1, Jan. 1, 1996, pp. 31–34; XP000971535; Abstract p. 33, column 2, last paragraph–page 34, column 1, paragraph 2.

Database WPI; Section Ch, Week 200039, Derwent Publications Ltd., London, GB; Class B04, AN 2000–450226; XP002155728 & RU 2 139 346 C (Shenderov B A), Oct. 10, 1999; Abstract.

Hokama Sanehiro et al; "Oxalate–degrading Enterococcus Faecalis", Microbiology and Immunology; vol. 44, No. 4, 2000, pp. 235–240; XP000971542; ISSN: 0385–5600; Abstract; p. 235, column 2; p. 237, paragraph 3; p. 238, column 1, last paragraph–column 2, paragraph 1; p. 239, paragraph 2.

*Primary Examiner*—Jean C. Witz
(74) *Attorney, Agent, or Firm*—Nixon & Vanderhye P.C.

(57) ABSTRACT

This invention provides materials and procedures for the delivery of selected strains of bacteria and/or oxalate-degrading enzymes to the intestinal tracts of persons who are at increased risk for oxalate related disease because they have lost, or have inadequate concentrations of these bacteria. The administration of these bacteria and/or the relevant enzyme removes oxalate from the intestinal tract and thus reduces the amount of oxalate available for absorption and reduces the risk for oxalate related disease.

5 Claims, No Drawings

DIETARY OR PHARMACEUTICAL COMPOSITION FOR USE FOR THE PREVENTION OR TREATMENT OF HYPEROXALURIA

This application is a continuation of Application No. PCT/IT00/00213, filed May 24, 1999 the entire content of which is hereby incorporated by reference in this application.

The present invention relates to the use of bacterial species and/or strains that will be indicated later, for preparing a composition for the prevention and/or treatment of hyperoxaluria and of disorders associated with this, as well as the composition thus obtained.

Correspondingly, the said composition can assume the form and perform the activity of a dietary composition or of a food supplement or of a real drug, depending on the supporting or preventive or truly therapeutic action that the composition is intended to exert depending on the particular individuals for whom it is intended. This preventive or truly therapeutic action can derive from colonization, by the said bacteria, of the intestine of subjects at risk of hyperoxaluria or disorders associated with hyperoxaluria.

Hyperoxaluria consists of excessive presence of oxalates in the urine (urinary oxalate >40 mg/die). As well as being caused by a genetic defect that alters the metabolism of glyoxylic acid with formation of oxalate instead of glycine, it may be a side effect of excessive ingestion of foods rich in oxalate, such as spinach, cocoa, hazelnuts, pepper and tea, or treatment with, for example, anti-obesity drugs (e.g. ORLISTAT). Hence the usefulness of providing a dietary supplement capable of reducing and regulating the presence of oxalates in the urine.

Hyperoxaluria is a predominantrisk factor for the formation of renal calculi and may be caused by excessive absorption of oxalate from the colon or by renal overload caused by hyperoxaluria as in primary hyperoxaluria (PH).

The urinary level of oxalate seems to constitute a crucial sign with regard to the formation of calcium oxalate calculi even in patients with normal urinary excretion of calcium, and calcium oxalate calculi can sometimes also form in patients under strictly oliguric dialysis and without a prior history of nephrolithic disease in that, within this framework, there may be oxalate supersaturation even in a minimal quantity of urine.

The daily excretion of oxalate is related to urinary volume, to the taking of vitamin C, to the body weight index and, inversely, to the intake of calcium.

A study by Sutton and Walker on a population of idiopathic calcium oxalate calculi formers with slight hyperoxaluria was unable to demonstrate any significant alteration of renal control of oxalate, and concluded there was an increased dietary burden of oxalate with a possible hyperabsorption mechanism.

In non-PH hyperoxaluria patients it will therefore be necessary to pay greatest attention to enteral hyperabsorption of oxalate, which promotes the clinical picture of enteric hyperoxaluria and often the recurrent production of renal calculi. It has in fact been recognized since 1968 that nephrolithiasis is a complication of a disease or of resection of the intestine.

Increased intestinal absorption of oxalate, termed enteric hyperoxaluria (EHO), depends on at least two mechanisms. The first is associated with malabsorption of biliary salts in the diseased or resected ileum, which causes a deficiency of biliary salts and malabsorption of fats. Most of the oxalate in the diet is bound to calcium and is scarcely absorbed, but poorly absorbed fats bind intraluminal calcium, lowering the quantity bound to oxalate and giving rise to increased absorption of oxalate. The second mechanism of EHO is associated with increased permeability of the colon for oxalate, caused by poorly absorbed fatty acids and biliary salts, perhaps aggravated by variations of the epithelial occluding junctions of the colon caused by the decrease in intraluminal calcium. This hyperoxaluria is related to the degree of steatorrhoea, and is unusual with ileal resections <30 cm. A decreased count of bacteria that metabolize the colon oxalate (*Oxalobacter formigenes*) as well as their inhibition by poorly absorbed biliary salts can likewise contribute to EHO. Finally, hyperoxaluria can be observed with long-term parenteral nutrition, also in patients with colectomies and minimal intake by the oral route, perhaps because of increased synthesis of endogenous oxalate.

Oxalate is sparingly soluble in water, but the urine can become supersaturated through the presence of crystallization inhibitors. Hyperoxaluria, combined with a decreased volume of urine and reduced levels of these inhibitors, predisposes to renal calculi.

Parenchymal renal deposition of oxalate can cause interstitial nephritis and nephrocalcinosis, with acute or chronic renal insufficiency.

The treatment of patients with calcium oxalate calculi is complex, and is described below.

Stage 1

Increased intake of liquids for a urinary excretion of 3 l/day;

Diet low in oxalate (avoid spinach, rhubarb, beets, hazelnuts, tea, cola, chocolate, wheat bran, strawberries);

Low-fat diet (50 g/day);

Calcium supplement (1–2 g/day);

Cholestyramine (4 g four times a day);

Stage 2 (if Calculi Recur Despite the Treatment of Stage 1)

Alkalization of the urine and citrate supplement (for example potassium citrate, sodium citrate=30 mEq base four times a day);

Magnesium supplement (to correct the urinary levels);

Allopurinol 300 mg/day (if the calculi contain uric acid).

The possibility of gastroenteric biological manipulation of oxalate had been known since 1955 from documents on the destruction of oxalate by the contents of the cow rumen and, subsequently, by mixed bacterial flora of the large intestine of other herbivores.

Allison referred in 1985 to the specific effect of degradation of oxalate of *Oxalobacter formigenes*, which inhabits the large intestine of man as well as of other animals.

More recently, Ito demonstrated the degradation of the oxalate content of foods in vitro by means of *Eubacterium lentum* WIH-1.

Subsequently, the absence of *Oxalobacter formigenes* was suggested as a risk factor for hyperoxaluria in cystic fibrosis patients.

Enteric hyperoxaluria is therefore the result of excessive enteric absorption of oxalate through increased permeability of the mucosa or increased solubility and bioavailability of faecal oxalate such as when the calcium content of the diet is reduced. The absence of *Oxalobacter formigenes* can add a new pathophysiological mechanism that is important from the standpoint of therapy.

Now it has been found, surprisingly, that the following bacteria: *Streptococcus thermophilus, Lactobacillus brevis, Lactobacillus acidophilus, Lactobacillus plantarum, Bifidobacterium infantis, Bifidobacterium longum* and *Bifidobacterium breve* are capable of growing in the presence of and/or of degrading oxalate.

Accordingly, the present invention provides the use of at least one strain of the following bacteria: *Streptococcus thermophilus, Lactobacillus brevis, Lactobacillus acidophilus, Lactobacillus plantarum, Bifidobacterium infantis, Bifidobacterium longum* and *Bifidobacterium breve* for preparing a dietary and/or pharmaceutical composition for the prevention and/or treatment of hyperoxaluria and the disorders associated with this.

Preferably, the strain of *Lactobacillus brevis* is the strain of *Lactobacillus brevis* CD2 deposited at the DSM— Deutsche Sammlung von Mikroorganismen und Zellkulturen GmbH, Braunschweig, Germany, on Feb. 6, 1998 with accession number DSM 11988 under the Budapest Treaty, or mutants and derivatives thereof.

More particularly, hyperoxaluria and the disorders associated with it comprise enteric hyperoxaluria, renal calcium oxalate lithiasis, hyperoxalurias from intestinal inflammatory diseases, renal insufficiency, vesical calculosis, cardiopathy from hyperoxaluria, cystic fibrosis and vulvodynia.

Use of the invention includes use in the veterinary field.

According to the invention, the dietary and/or pharmaceutical composition is able to colonize, with the said bacteria, the intestine of subjects at risk of hyperoxaluria or disorders from hyperoxaluria, or disorders from renal calcium oxalate lithiasis.

The invention likewise provides a dietary or pharmaceutical composition comprising at least one strain of the following bacteria: *Streptococcus thermophilus, Lactobacillus brevis, Lactobacillus acidophilus, Lactobacillus plantarum, Bifidobacterium infantis, Bifidobacterium longum* and *Bifidobacterium breve*.

According to one embodiment of the invention, a strain of *Streptococcus thermophilus* is combined with a strain of Lactobacilius selected from the group consisting of *Lactobacillus brevis, Lactobacillus acidophilus* and *Lactobacillus plantarum* or their mixtures. Preferably, the strain of *Lactobacillus brevis* is the strain of *Lactobacillus brevis* CD2 deposited at the DSM—Deutsche Sammlung von Mikroorganismen und Zellkulturen GmbH, Braunschweig, Germany, on Feb. 6, 1998 with accession number DSM 11988 under the Budapest Treaty, or mutants and derivatives thereof.

According to another embodiment of the invention, a strain of *Streptococcus thermophilus* is combined with a strain of Bifidobacterium selected from the group consisting of *Bifidobacterium infantis, Bifidobacterium longum* and *Bifidobacterium breve* or their mixtures. In this case, preferably, the proportions between the concentrations of *Bifidobacterium infantis, Bifidobacterium longum* and *Bifidobacterium breve* in the mixture, expressed in CFU/g of composition, are preferably 1:1:1.

According to a preferred embodiment, the ratio between the concentrations of *Streptococcus thermophilus* and of the bacterium of the genus Lactobacillus, expressed in CFU/g of composition, is from 1000:1 to 1:1000, whereas the ratio between the concentrations of *Streptococcus thermophilus* and of the bacterium of the genus Bifidobacterium or the mixture of bacteria of the genus Bifidobacterium, expressed in CFU/g of composition, is from 1000:1 to 1:1000.

The total concentration of the bacteria is preferably from $10^6$ to $10^{12}$ CFU/g of composition.

According to the invention, the composition can moreover contain or be administered in combination with:

substances capable of binding the oxalate in the intestinal lumen, in particular cholestyramine (for example 0.5–4 g/die) and organic hydrocolloids of marine origin, vitamins, in particular $B_6$ (for example 20–200 mg/die) and C (for example 0.1–2 g/die), magnesium oxide (for example 50–600 mg/die), calcium (for example 0.5–2 g/die), allopurinol (for example 50–300 mg/die), enzymes, lactic bacteria, hormones and diuretics, immunomodulators, anticancer, lipids, urine alkalizers, urine acidifiers, saturated and unsaturated fatty acids and phospholipids, drugs bringing about hyperoxaluria as a side effect, for example anti-obesity drugs (e.g. ORLISTAT).

Generally the composition can be administered orally or by the intraluminal route or by enteroclysis in the form of granules, tablets, capsules, suppositories or by enteroclysm.

The invention also provides a food based on chocolate, cocoa, asparagus, tomato, drinks/liquids, spinach, walnuts, hazelnuts, fibres, cereals, potato, tea and peanut butter, containing a quantity of at least one strain of bacteria selected from among *Streptococcus thermophilus, Lactobacillus brevis, Lactobacillus acidophilus, Lactobacillus plantarum, Bifidobacterium infantis, Bifidobacterium longum* and *Bifidobacterium breve*, sufficient to colonize the intestine of subjects at risk of hyperoxaluria or disorders arising from hyperoxaluria.

The invention finally provides a method for the prevention and/or treatment of hyperoxaluria and the disorders associated with this by administering, to a subject at risk of hyperoxaluria or a disorder arising from hyperoxaluria, from 0.5 to 4 g/die of the composition of any one of the claims from 4 to 10.

"Subjects" in this context includes humans and animals in general, and in particular farm animals, sport animals and pets.

EXAMPLE 1

Pure Cultures

Bifidobacterium infantis, Lactobacillus acidophilus, Lactobacillus plantarum, Lactobacillus brevisand *Streptococcus thermophilus* were employed for the following experiment.

All the strains were stored lyophilized in a refrigerated environment. *Bifidobacterium infantis* was cultivated in MRS broth (DIFCO)+0.5% glucose, incubated anaerobically at 37° C. for 18 hours in Gas Pak with atmosphere of $CO_2$ and $H_2$, the *Lactobacillus acidophilus* and *Lactobacillus plantarum* in MRS (DIFCO) broth, incubated at 37° C. for 18 hours, the *Lactobacillus brevis* in MRS (DIFCO) broth, incubated at 30° C. for 18 hours, and the *Streptococcus thermophilus* in MI7 (DIFCO) broth+0.5% of lactose and incubated at 37° C. for 18 hours.

Media

For preparation of the culture media containing ammonium oxalate (BDH) 10 mM and 20 mM, to 10 ml of base medium (formulated as follows: 10 g of proteoses peptone No. 3 (DIFCO)+5 g of yeast extract (DIFCO)+1 ml of Tween '80 (DIFCO)+2 g of $KH_2PO_4$ (BDH)+5 g of sodium acetate (BDH)+2 g of ammonium dihydrogencitrate (MERCK)+0.05 g of $MgSO_4.7H_2O$ (MERCK)+0.05 g of $MnSO_4$ (MERCK)+water qs. to 500 ml and sterilized at 121° C. for 15 min) 10 ml of the following sugars and ammonium oxalate solutions, sterilized with 0.45 µm filter, were added, and namely:

for *L. acidophilus, L. plantarum* and *L. brevis*

1A: ammonium oxalate 20 mM+40 g/l of glucose (BDH)

1B: ammonium oxalate 40 mM+40 g/l of glucose for *S. thermophilus*

2A: ammonium oxalate 20 mM+40 g/l of glucose+10 g/l of lactose (DIFCO)

2B: ammonium oxalate 40 mM+40 g/l of glucose+10 g/l of lactose for *B. infantis*

3A: ammonium oxalate 20 mM+50 g/l of glucose

3B: ammonium oxalate 40 mM+50 g/l of glucose

After mixing, the samples labelled A contain ammonium oxalate 10 mM, whereas the samples labelled B contain ammonium oxalate 20 mM.

The culture broths were then inoculated at 10% with a fresh culture and incubated in the appropriate conditions of each strain described above.

Each grown broth culture was submitted to counting of the number of microorganisms contained in the culture media in the appropriate conditions, and in particular:

*B. infantis* in agar HHD (HI Media Laboratories), incubated anaerobically at 37° C. for 3 days;

*L. acidophilus* in agar MRS (DIFCO), incubated anaerobically at 37° C. for 3 days;

*L. plantarum* and *L. brevis* in agar MRS (DIFCO), incubated anaerobically at 37° C. for 3 days;

*S. thermophilus* in agar MI7 (DIFCO), incubated at 37° C. for 2 days.

Determination of Oxalic Acid

Sample Preparation

Broth cultures were pasteurized at 90° C. for 15 min, then centrifuged at 5000 rpm for 10 min, and finally the supernatant was filtered with a 0.45 μm filter.

Method

The oxalic acid content was determined with the "Oxalic acid" kit (Boehringer Mannheim) specific for this acid. The analysis was performed with a spectrophotometer (Perkin Elmer—Lambda 5) at 340 nm.

Results

As can be seen from Table 1 below, all the strains generally develop in the presence of ammonium oxalate 10 mM, whereas a concentration of 20 mM partly inhibits microbial growth, especially in the case of *L. acidophilus* and *S. thermophilus*.

However, there does not seem to be a relation between bacterial development and degradation of the oxalate. Thus, *L. plantarum* and *L. brevis* cause little if any degradation of the oxalate, even if they display significant growth.

On the other hand, *L. acidophilus* and *S. thermophilus* degrade the oxalate at both concentrations, despite the reduced growth in the presence of ammonium oxalate 20 mM. *B. infantis*, finally, exhibits very good degradation activity and is not inhibited by the oxalate at either concentration.

TABLE 1

| Oxalic acid | 10 mM | | | 20 mM | | |
|---|---|---|---|---|---|---|
| | Degradation (%) | Microbial content (CFU/ml × 10$^6$) | | Degradation (%) | Microbial content (CFU/ml × 10$^6$) | |
| | | $t_0$ | Final growth | | $t_0$ | Final growth |
| *L. brevis* | 0.94 | 27 | 130 | 0.73 | 27 | 120 |
| *L. acidophilus* | 11.79 | 25 | 130 | 3.41 | 25 | 52 |
| *L. plantarum* | 1.42 | 32 | 270 | 0.00 | 32 | 230 |

TABLE 1-continued

| Oxalic acid | 10 mM | | | 20 mM | | |
|---|---|---|---|---|---|---|
| | Degradation (%) | Microbial content (CFU/ml × 10$^6$) | | Degradation (%) | Microbial content (CFU/ml × 10$^6$) | |
| | | $t_0$ | Final growth | | $t_0$ | Final growth |
| *S. thermophilus* | 2.31 | 2.5 | 26 | 3.06 | 2.5 | 9 |
| *B. infantis* | 5.26 | 36 | 300 | 2.18 | 36 | 230 |

EXAMPLE 2

Cases

After informed consent, 7 patients with hyperoxaluria were administered *Streptococcus thermophilus* orally 6 g per day for 3 weeks, and oxaluria was determined in 24 hours at time 0 and after 3 weeks.

The oxalate in urine was determined by standard methods employed in clinical chemistry and expressed as mg of oxalate in urine collected in a period of time of 24 hours.

After 3 weeks, the oxalaemia results were as follows:

| Patient | Before | After |
|---|---|---|
| 1 | 50 | 7 |
| 2 | 47 | 30 |
| 3 | 41 | 31 |
| 4 | 95 | 56 |
| 5 | 62 | 14 |
| 6 | 58 | 34 |
| 7 | 49 | 12 |

It is clear that in patients with high levels of oxalate in the urine, the treatment brought about a notable reduction of the oxalate levels.

What is claimed is:

1. A method for the prophylaxis or treatment of hyperoxaluria and the disorders associated therewith which comprises administering to an animal in need thereof from 0.5 to 4 g/day of a bacterial combination composition comprising:
    (a) *Streptococcus thermophilus* in admixture with
    (b) at least one bacterial strain selected from the group consisting of *Lactobacillus brevis, Lactobacillus acidophilus, Lactobacillus plantarum, Bifidobacterium infantis, Bifidobacterium longum* and *Bifidobacterium breve* or mixtures thereof.

2. The method of claim 1, wherein the strain of *Lactobacillus brevis* is DSM 11988 or mutants and derivatives thereof.

3. The method of claim 1, wherein the ratio of the concentrations of *Bifidobacterium infantis, Bifidobacterium longum* and *Bifidobacterium breve* in the mixture, expressed in CFU/g of composition, are 1:1:1.

4. The method of claim 1, wherein the ratio of the concentrations of *Streptococcus thermophilus* and the Lactobacillus strain, expressed in CFU/g of composition, is from 1000:1 to 1:1000.

5. The method of claim 1, wherein the ratio of the concentrations of *Streptococcus thermophilus* and the Bifidobacterium strain, expressed in CFU/g of composition, is from 1000:1 to 1:1000.

* * * * *

UNITED STATES PATENT AND TRADEMARK OFFICE
CERTIFICATE OF CORRECTION

PATENT NO.    : 6,562,336 B2                                              Page 1 of 1
DATED         : May 13, 2003
INVENTOR(S)   : Claudio De Simone It is certified that error appears in the above-identified patent and that said Letters Patent is hereby corrected as shown below:

<u>Title page,</u>
Item [30], Foreign Application Priority Data

Signed and Sealed this

Sixth Day of April, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,562,336 B2
DATED : May 13, 2003
INVENTOR(S) : De Simone, Claudio

It is certified that error appears in the above-identified patent and that said Letters Patent is hereby corrected as shown below:

Title page,
Item [30], Foreign Application Priority Data, should read
-- May 28, 1999    (IT)        RM99A000338 --
Item [63], Signed and Sealed this Fourteenth Day of September, 2004

JON W. DUDAS
*Director of the United States Patent and Trademark Office*

UNITED STATES PATENT AND TRADEMARK OFFICE
CERTIFICATE OF CORRECTION

PATENT NO. : 6,562,336 B2
DATED : May 13, 2003
INVENTOR(S) : De Simone, Claudio

It is certified that error appears in the above-identified patent and that said Letters Patent is hereby corrected as shown below:

Title page,
Item [30], Foreign Application Priority Data, should read
-- May 28, 1999    (IT)         RM99A000338 --
Item [63], should read -- Continuation of application No. PCT/IT00/00213, filed on May 24, 2000. --

Column 8,
Line 5, claim 8 should read as follows:

> 8. (Amended) A method for the prophylaxis or treatment of hyperoxaluria and the disorders associated therewith which comprises administering to a subject in need thereof from 0.5 to 4 g/day of a bacterial combination composition comprising:
>
> (a) *Streptococcus thermophilus* in admixture with
>
> (b) at least one bacterial strain selected from the group consisting of *Lactobacillus brevis, Lactobacillus acidophilus, Lactobacillus plantarum, Bifidobacterium infantis, Bifidobacterium longum* and *Bifidobacterium breve* or mixtures thereof.

Add the following new claims:
-- 13. (new) The method of claim 8, wherein the subject is a human.

14. (new) The method of claim 8, wherein the subject is an animal. --

This certificate supersedes Certificate of Correction issued April 6, 2004 and September 14, 2004. --

Signed and Sealed this

Sixteenth Day of November, 2004

JON W. DUDAS
*Director of the United States Patent and Trademark Office*